(12) United States Patent
Arizaga Ballesteros

(10) Patent No.: US 7,574,245 B2
(45) Date of Patent: Aug. 11, 2009

(54) FLEXIBLE MEDICAL SENSOR ENCLOSURE

(75) Inventor: Adolfo Arizaga Ballesteros, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 357 days.

(21) Appl. No.: 11/528,293

(22) Filed: Sep. 27, 2006

(65) Prior Publication Data

US 2008/0076987 A1 Mar. 27, 2008

(51) Int. Cl.
*A61B 5/1455* (2006.01)
(52) U.S. Cl. .......................................... 600/344; 53/461
(58) Field of Classification Search ................. 600/322, 600/323, 344; 53/461, 462; 24/306
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsey et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |

(Continued)

FOREIGN PATENT DOCUMENTS

DE 3405444 8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

(Continued)

*Primary Examiner*—Eric F Winakur
*Assistant Examiner*—Etsub D Berhanu
(74) *Attorney, Agent, or Firm*—Fletcher Yoder

(57) ABSTRACT

A sensor is provided that includes a flexible wrap enclosure which is folded about the sensor. The flexible wrap includes primary flaps and at least one reinforcement flap. The reinforcement flap may be used to enclose areas of the sensor not enclosed by the primary wrap and/or may be used to provide reinforcement of the enclosure to prevent tearing of the flexible wrap enclosure. The sensor may be placed on a patient's finger, toe, ear, and so forth to obtain pulse oximetry or other physiological measurements.

17 Claims, 6 Drawing Sheets

U.S. PATENT DOCUMENTS

| | | |
|---|---|---|
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE033,643 E | 7/1991 | Isaacson et al. |
| 5,028,787 A | 7/1991 | Rosenthal et al. |
| 5,035,243 A | 7/1991 | Muz |
| 5,040,039 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynksi |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |

| | | | | | |
|---|---|---|---|---|---|
| 5,349,519 A | 9/1994 | Kaestle | 5,575,285 A | 11/1996 | Takanashi et al. |
| 5,349,952 A | 9/1994 | McCarthy et al. | 5,577,500 A | 11/1996 | Potratz |
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,992 A | 4/1997 | Guthrie et al. |
| 5,372,136 A | 12/1994 | Steuer et al. | 5,626,140 A | 5/1997 | Feldman et al. |
| 5,377,675 A | 1/1995 | Ruskewicz et al. | 5,630,413 A | 5/1997 | Thomas et al. |
| 5,385,143 A | 1/1995 | Aoyagi | 5,632,272 A | 5/1997 | Diab et al. |
| 5,387,122 A | 2/1995 | Goldberger et al. | 5,632,273 A | 5/1997 | Suzuki |
| 5,390,670 A | 2/1995 | Centa et al. | 5,634,459 A | 6/1997 | Gardosi |
| 5,392,777 A | 2/1995 | Swedlow et al. | 5,638,593 A | 6/1997 | Gerhardt et al. |
| 5,398,680 A | 3/1995 | Polson et al. | 5,638,816 A | 6/1997 | Kiani-Azarbayjany et al. |
| 5,402,777 A | 4/1995 | Warring et al. | 5,638,818 A | 6/1997 | Diab et al. |
| 5,402,779 A | 4/1995 | Chen et al. | 5,645,060 A | 7/1997 | Yorkey et al. |
| 5,411,023 A | 5/1995 | Morris, Sr. et al. | 5,645,440 A | 7/1997 | Tobler et al. |
| 5,411,024 A | 5/1995 | Thomas et al. | 5,660,567 A | 8/1997 | Nierlich et al. |
| 5,413,099 A | 5/1995 | Schmidt et al. | 5,662,105 A | 9/1997 | Tien |
| 5,413,100 A | 5/1995 | Barthelemy et al. | 5,662,106 A | 9/1997 | Swedlow et al. |
| 5,413,101 A | 5/1995 | Sugiura | 5,664,270 A | 9/1997 | Bell et al. |
| 5,413,102 A | 5/1995 | Schmidt et al. | 5,666,952 A | 9/1997 | Fuse et al. |
| 5,417,207 A | 5/1995 | Young et al. | 5,671,529 A | 9/1997 | Nelson |
| 5,421,329 A | 6/1995 | Casciani et al. | 5,673,692 A | 10/1997 | Schulze et al. |
| 5,425,360 A | 6/1995 | Nelson | 5,673,693 A | 10/1997 | Solenberger |
| 5,425,362 A | 6/1995 | Siker et al. | 5,676,139 A | 10/1997 | Goldberger et al. |
| 5,427,093 A | 6/1995 | Ogawa et al. | 5,676,141 A | 10/1997 | Hollub |
| 5,429,128 A | 7/1995 | Cadell et al. | 5,678,544 A | 10/1997 | DeLonzor et al. |
| 5,429,129 A | 7/1995 | Lovejoy et al. | 5,680,857 A | 10/1997 | Pelikan et al. |
| 5,431,159 A | 7/1995 | Baker et al. | 5,685,299 A | 11/1997 | Diab et al. |
| 5,431,170 A | 7/1995 | Mathews | 5,685,301 A | 11/1997 | Klomhaus |
| 5,437,275 A | 8/1995 | Amundsen et al. | 5,687,719 A | 11/1997 | Sato et al. |
| 5,438,986 A | 8/1995 | Disch et al. | 5,687,722 A | 11/1997 | Tien et al. |
| 5,448,991 A | 9/1995 | Polson et al. | 5,692,503 A | 12/1997 | Kuenstner |
| 5,452,717 A | 9/1995 | Branigan et al. | 5,692,505 A | 12/1997 | Fouts |
| 5,465,714 A | 11/1995 | Scheuing | 5,709,205 A | 1/1998 | Bukta |
| 5,469,845 A | 11/1995 | DeLonzor et al. | 5,713,355 A | 2/1998 | Richardson et al. |
| RE035,122 E | 12/1995 | Corenman et al. | 5,724,967 A | 3/1998 | Venkatachalam |
| 5,482,034 A | 1/1996 | Lewis et al. | 5,727,547 A | 3/1998 | Levinson et al. |
| 5,482,036 A | 1/1996 | Diab et al. | 5,730,124 A | 3/1998 | Yamauchi |
| 5,485,847 A | 1/1996 | Baker, Jr. | 5,731,582 A | 3/1998 | West |
| 5,490,505 A | 2/1996 | Diab et al. | D393,830 S | 4/1998 | Tobler et al. |
| 5,490,523 A | 2/1996 | Isaacson et al. | 5,743,260 A | 4/1998 | Chung et al. |
| 5,491,299 A | 2/1996 | Naylor et al. | 5,743,262 A | 4/1998 | Lepper, Jr. et al. |
| 5,494,032 A | 2/1996 | Robinson et al. | 5,743,263 A | 4/1998 | Baker, Jr. |
| 5,494,043 A | 2/1996 | O'Sullivan et al. | 5,746,206 A | 5/1998 | Mannheimer |
| 5,497,771 A | 3/1996 | Rosenheimer | 5,746,697 A | 5/1998 | Swedlow et al. |
| 5,499,627 A | 3/1996 | Steuer et al. | 5,752,914 A | 5/1998 | DeLonzor et al. |
| 5,503,148 A | 4/1996 | Pologe et al. | 5,755,226 A | 5/1998 | Carim et al. |
| 5,505,199 A | 4/1996 | Kim | 5,758,644 A | 6/1998 | Diab et al. |
| 5,507,286 A | 4/1996 | Solenberger | 5,760,910 A | 6/1998 | Lepper, Jr. et al. |
| 5,511,546 A | 4/1996 | Hon | 5,766,125 A | 6/1998 | Aoyagi et al. |
| 5,517,988 A | 5/1996 | Gerhard | 5,766,127 A | 6/1998 | Pologe et al. |
| 5,520,177 A | 5/1996 | Ogawa et al. | 5,769,785 A | 6/1998 | Diab et al. |
| 5,521,851 A | 5/1996 | Wei et al. | 5,772,587 A | 6/1998 | Gratton et al. |
| 5,522,388 A | 6/1996 | Ishikawa et al. | 5,774,213 A | 6/1998 | Trebino et al. |
| 5,524,617 A | 6/1996 | Mannheimer | 5,776,058 A | 7/1998 | Levinson et al. |
| 5,529,064 A | 6/1996 | Rall et al. | 5,776,059 A | 7/1998 | Kaestle |
| 5,533,507 A | 7/1996 | Potratz et al. | 5,779,630 A | 7/1998 | Fein et al. |
| 5,551,423 A | 9/1996 | Sugiura | 5,779,631 A | 7/1998 | Chance |
| 5,551,424 A | 9/1996 | Morrison et al. | 5,782,237 A | 7/1998 | Casciani et al. |
| 5,553,614 A | 9/1996 | Chance | 5,782,756 A | 7/1998 | Mannheimer |
| 5,553,615 A | 9/1996 | Carim et al. | 5,782,757 A | 7/1998 | Diab et al. |
| 5,555,882 A | 9/1996 | Richardson et al. | 5,782,758 A | 7/1998 | Ausec et al. |
| 5,558,096 A | 9/1996 | Palatnik | 5,786,592 A | 7/1998 | Hök |
| 5,560,355 A | 10/1996 | Merchant et al. | 5,788,634 A | 8/1998 | Suda et al. |
| 5,564,417 A | 10/1996 | Chance | 5,790,729 A | 8/1998 | Pologe et al. |
| 5,575,284 A | 11/1996 | Athan et al. | 5,792,052 A | 8/1998 | Isaacson et al. |

| | | | | | |
|---|---|---|---|---|---|
| 5,795,292 A | 8/1998 | Lewis et al. | 5,987,343 A | 11/1999 | Kinast |
| 5,797,841 A | 8/1998 | DeLonzor et al. | 5,991,648 A | 11/1999 | Levin |
| 5,800,348 A | 9/1998 | Kaestle | 5,995,855 A | 11/1999 | Kiani et al. |
| 5,800,349 A | 9/1998 | Isaacson et al. | 5,995,856 A | 11/1999 | Mannheimer et al. |
| 5,803,910 A | 9/1998 | Potratz | 5,995,858 A | 11/1999 | Kinast |
| 5,807,246 A | 9/1998 | Sakaguchi et al. | 5,995,859 A | 11/1999 | Takahashi |
| 5,807,247 A | 9/1998 | Merchant et al. | 5,997,343 A | 12/1999 | Mills et al. |
| 5,807,248 A | 9/1998 | Mills | 5,999,834 A | 12/1999 | Wang et al. |
| 5,810,723 A | 9/1998 | Aldrich | 6,002,952 A | 12/1999 | Diab et al. |
| 5,810,724 A | 9/1998 | Gronvall | 6,005,658 A | 12/1999 | Kaluza et al. |
| 5,813,980 A | 9/1998 | Levinson et al. | 6,006,120 A | 12/1999 | Levin |
| 5,817,008 A | 10/1998 | Rafert et al. | 6,011,985 A | 1/2000 | Athan et al. |
| 5,817,009 A | 10/1998 | Rosenheimer et al. | 6,011,986 A | 1/2000 | Diab et al. |
| 5,817,010 A | 10/1998 | Hibl | 6,014,576 A | 1/2000 | Raley et al. |
| 5,818,985 A | 10/1998 | Merchant et al. | 6,018,673 A | 1/2000 | Chin et al. |
| 5,820,550 A | 10/1998 | Polson et al. | 6,018,674 A | 1/2000 | Aronow |
| 5,823,950 A | 10/1998 | Diab et al. | 6,022,321 A | 2/2000 | Amano et al. |
| 5,823,952 A | 10/1998 | Levinson et al. | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE036,000 E | 12/1998 | Swedlow et al. | 6,047,201 A | 4/2000 | Jackson, III |
| 5,842,979 A | 12/1998 | Jarman et al. | 6,055,447 A | 4/2000 | Well |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjani et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura et al. |
| 5,924,982 A | 7/1999 | Chin | 6,157,850 A | 12/2000 | Diab et al. |
| 5,924,985 A | 7/1999 | Jones | 6,159,147 A | 12/2000 | Lichter |
| 5,934,277 A | 8/1999 | Mortz | 6,163,175 A | 12/2000 | Larsen et al. |
| 5,934,925 A | 8/1999 | Tobler et al. | 6,163,715 A | 12/2000 | Larsen et al. |
| 5,940,182 A | 8/1999 | Lepper, Jr. et al. | 6,165,005 A | 12/2000 | Mills et al. |
| 5,954,644 A | 9/1999 | Dettling et al. | 6,173,196 B1 | 1/2001 | Delonzor et al. |
| 5,957,840 A | 9/1999 | Terasawa et al. | 6,178,343 B1 | 1/2001 | Bindszus et al. |
| 5,960,610 A | 10/1999 | Levinson et al. | 6,179,159 B1 | 1/2001 | Gurley |
| 5,961,450 A | 10/1999 | Merchant et al. | 6,181,958 B1 | 1/2001 | Steuer et al. |
| 5,961,452 A | 10/1999 | Chung et al. | 6,181,959 B1 | 1/2001 | Schöllerman et al. |
| 5,964,701 A | 10/1999 | Asada et al. | 6,184,521 B1 | 2/2001 | Coffin, IV et al. |
| 5,971,930 A | 10/1999 | Elghazzawi | 6,188,470 B1 | 2/2001 | Grace |
| 5,978,691 A | 11/1999 | Mills | 6,192,260 B1 | 2/2001 | Chance |
| 5,978,693 A | 11/1999 | Hamilton et al. | 6,195,575 B1 | 2/2001 | Levinson |
| 5,983,120 A | 11/1999 | Groner et al. | 6,198,951 B1 | 3/2001 | Kosuda et al. |
| 5,983,122 A | 11/1999 | Jarman et al. | 6,206,830 B1 | 3/2001 | Diab et al. |

| | | |
|---|---|---|
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B1 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |

| | | |
|---|---|---|
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE038,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE038,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,971,580 B2 | 12/2005 | DeLonzor et al. |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |

| | | | | | | |
|---|---|---|---|---|---|---|
| 7,047,055 | B2 | 5/2006 | Boaz et al. | 2004/0024297 A1 | 2/2004 | Chen et al. |
| 7,060,035 | B2 | 6/2006 | Wasserman et al. | 2004/0024326 A1 | 2/2004 | Yeo et al. |
| 7,062,307 | B2 | 6/2006 | Norris et al. | 2004/0034293 A1 | 2/2004 | Kimball |
| 7,067,893 | B2 | 6/2006 | Mills et al. | 2004/0039272 A1 | 2/2004 | Abdul-Hafiz et al. |
| 7,072,701 | B2 | 7/2006 | Chen et al. | 2004/0039273 A1 | 2/2004 | Terry |
| 7,072,702 | B2 | 7/2006 | Edgar, Jr. et al. | 2004/0054269 A1 | 3/2004 | Rantala et al. |
| 7,079,880 | B2 | 7/2006 | Stetson | 2004/0054291 A1 | 3/2004 | Schulz et al. |
| 7,085,597 | B2 | 8/2006 | Fein et al. | 2004/0059209 A1 | 3/2004 | Al-Ali et al. |
| 7,096,052 | B2 | 8/2006 | Mason et al. | 2004/0059210 A1 | 3/2004 | Stetson |
| 7,096,054 | B2 | 8/2006 | Abdul-Hafiz et al. | 2004/0064020 A1 | 4/2004 | Diab et al. |
| 7,107,088 | B2 | 9/2006 | Aceti | 2004/0068164 A1 | 4/2004 | Diab et al. |
| 7,113,815 | B2 | 9/2006 | O'Neil et al. | 2004/0087846 A1 | 5/2004 | Wasserman |
| 7,123,950 | B2 | 10/2006 | Mannheimer | 2004/0092805 A1 | 5/2004 | Yarita |
| 7,127,278 | B2 | 10/2006 | Melker et al. | 2004/0097797 A1 | 5/2004 | Porges et al. |
| 7,130,671 | B2 | 10/2006 | Baker, Jr. et al. | 2004/0098009 A1 | 5/2004 | Boecker et al. |
| 7,132,641 | B2 | 11/2006 | Schulz et al. | 2004/0107065 A1 | 6/2004 | Al-Ali et al. |
| 7,133,711 | B2 | 11/2006 | Chernoguz et al. | 2004/0116788 A1 | 6/2004 | Chernoguz et al. |
| 7,139,559 | B2 | 11/2006 | Terry | 2004/0116789 A1 | 6/2004 | Boaz et al. |
| 7,142,901 | B2 | 11/2006 | Kiani et al. | 2004/0117891 A1 | 6/2004 | Hannula et al. |
| 7,162,288 | B2 | 1/2007 | Nordstrom | 2004/0122300 A1 | 6/2004 | Boas et al. |
| 7,190,987 | B2 | 3/2007 | Lindekugel et al. | 2004/0122302 A1 | 6/2004 | Mason et al. |
| 7,198,778 | B2 | 4/2007 | Mannheimer et al. | 2004/0133087 A1 | 7/2004 | Ali et al. |
| 7,215,984 | B2 | 5/2007 | Diab et al. | 2004/0133133 A1 | 7/2004 | Al-Ali et al. |
| 7,225,006 | B2 | 5/2007 | Al-Ali et al. | 2004/0138538 A1 | 7/2004 | Stetson |
| 7,228,161 | B2 | 6/2007 | Chin | 2004/0138540 A1 | 7/2004 | Baker, Jr. et al. |
| 7,236,881 | B2 | 6/2007 | Schmitt et al. | 2004/0143172 A1 | 7/2004 | Fudge et al. |
| 7,248,910 | B2 | 7/2007 | Li et al. | 2004/0147821 A1 | 7/2004 | Al-Ali et al. |
| 7,254,433 | B2 | 8/2007 | Diab et al. | 2004/0147822 A1 | 7/2004 | Al-Ali et al. |
| 7,254,434 | B2 | 8/2007 | Schulz et al. | 2004/0147823 A1 | 7/2004 | Kiani et al. |
| 7,280,858 | B2 | 10/2007 | Al-Ali et al. | 2004/0147824 A1 | 7/2004 | Diab et al. |
| 7,295,866 | B2 | 11/2007 | Al-Ali et al. | 2004/0152965 A1 | 8/2004 | Diab et al. |
| 7,305,262 | B2 | 12/2007 | Brodnick et al. | 2004/0158134 A1 | 8/2004 | Diab et al. |
| 7,315,753 | B2 | 1/2008 | Baker, Jr. et al. | 2004/0158135 A1 | 8/2004 | Baker, Jr. et al. |
| 2001/0021803 | A1 | 9/2001 | Blank et al. | 2004/0162472 A1 | 8/2004 | Berson et al. |
| 2001/0051767 | A1 | 12/2001 | Williams et al. | 2004/0167381 A1 | 8/2004 | Lichter |
| 2002/0016537 | A1 | 2/2002 | Muz et al. | 2004/0171920 A1 | 9/2004 | Mannheimer et al. |
| 2002/0026109 | A1 | 2/2002 | Diab et al. | 2004/0171948 A1 | 9/2004 | Terry |
| 2002/0028990 | A1 | 3/2002 | Shepherd | 2004/0176671 A1 | 9/2004 | Fine et al. |
| 2002/0038078 | A1 | 3/2002 | Ito | 2004/0181133 A1 | 9/2004 | Al-Ali et al. |
| 2002/0042558 | A1 | 4/2002 | Mendelson | 2004/0181134 A1 | 9/2004 | Baker, Jr. et al. |
| 2002/0068859 | A1 | 6/2002 | Knopp | 2004/0186358 A1 | 9/2004 | Chernow et al. |
| 2002/0072681 | A1 | 6/2002 | Schnall | 2004/0199063 A1 | 10/2004 | O'Neil et al. |
| 2002/0116797 | A1 | 8/2002 | Modgil et al. | 2004/0204636 A1 | 10/2004 | Diab et al. |
| 2002/0128544 | A1 | 9/2002 | Diab et al. | 2004/0204637 A1 | 10/2004 | Diab et al. |
| 2002/0133067 | A1 | 9/2002 | Jackson, III | 2004/0204638 A1 | 10/2004 | Diab et al. |
| 2002/0156354 | A1 | 10/2002 | Larson | 2004/0204639 A1 | 10/2004 | Casciani et al. |
| 2002/0165440 | A1* | 11/2002 | Mason et al. ............ 600/344 | 2004/0204865 A1 | 10/2004 | Lee et al. |
| 2002/0173706 | A1 | 11/2002 | Takatani | 2004/0210146 A1 | 10/2004 | Diab et al. |
| 2002/0173709 | A1 | 11/2002 | Fine et al. | 2004/0215069 A1 | 10/2004 | Mannheimer |
| 2002/0190863 | A1 | 12/2002 | Lynn | 2004/0215085 A1 | 10/2004 | Schnall |
| 2002/0198442 | A1 | 12/2002 | Rantala et al. | 2004/0230107 A1 | 11/2004 | Asada et al. |
| 2003/0018243 | A1 | 1/2003 | Gerhardt et al. | 2004/0230108 A1 | 11/2004 | Melker et al. |
| 2003/0036690 | A1 | 2/2003 | Geddes et al. | 2004/0236196 A1 | 11/2004 | Diab et al. |
| 2003/0045785 | A1 | 3/2003 | Diab et al. | 2004/0242980 A1 | 12/2004 | Kiani et al. |
| 2003/0073889 | A1 | 4/2003 | Keilbach et al. | 2004/0249252 A1 | 12/2004 | Fine et al. |
| 2003/0073890 | A1 | 4/2003 | Hanna | 2004/0257557 A1 | 12/2004 | Block et al. |
| 2003/0100840 | A1 | 5/2003 | Sugiura et al. | 2004/0260161 A1 | 12/2004 | Melker et al. |
| 2003/0132495 | A1 | 7/2003 | Mills et al. | 2004/0267103 A1 | 12/2004 | Li et al. |
| 2003/0135099 | A1 | 7/2003 | Al-Ali | 2004/0267104 A1 | 12/2004 | Hannula et al. |
| 2003/0162414 | A1 | 8/2003 | Schulz et al. | 2004/0267140 A1 | 12/2004 | Ito et al. |
| 2003/0171662 | A1 | 9/2003 | O'Connor et al. | 2005/0004479 A1 | 1/2005 | Townsend et al. |
| 2003/0176776 | A1 | 9/2003 | Huiku | 2005/0010092 A1 | 1/2005 | Weber et al. |
| 2003/0181799 | A1 | 9/2003 | Lindekugel et al. | 2005/0014999 A1 | 1/2005 | Rahe-Meyer |
| 2003/0187337 | A1 | 10/2003 | Tarassenko et al. | 2005/0020887 A1 | 1/2005 | Goldberg |
| 2003/0195402 | A1 | 10/2003 | Fein et al. | 2005/0020894 A1 | 1/2005 | Norris et al. |
| 2003/0197679 | A1 | 10/2003 | Ali et al. | 2005/0033128 A1 | 2/2005 | Ali et al. |
| 2003/0212316 | A1 | 11/2003 | Leiden et al. | 2005/0033129 A1 | 2/2005 | Edgar, Jr. et al. |
| 2003/0225323 | A1 | 12/2003 | Kiani et al. | 2005/0033131 A1 | 2/2005 | Chen |
| 2003/0225337 | A1 | 12/2003 | Scharf et al. | 2005/0043599 A1 | 2/2005 | O'Mara |
| 2003/0236452 | A1 | 12/2003 | Melker et al. | 2005/0043600 A1 | 2/2005 | Diab et al. |
| 2003/0236647 | A1 | 12/2003 | Yoon et al. | 2005/0049468 A1 | 3/2005 | Carlson |
| 2004/0006261 | A1 | 1/2004 | Swedlow et al. | 2005/0049470 A1 | 3/2005 | Terry |
| 2004/0010188 | A1 | 1/2004 | Wasserman et al. | 2005/0049471 A1 | 3/2005 | Aceti |

| | | | | | | |
|---|---|---|---|---|---|---|
| 2005/0070773 | A1 | 3/2005 | Chin | EP | 01491135 A2 | 12/2004 |
| 2005/0075546 | A1 | 4/2005 | Samsoondar | FR | 2685865 | 1/1992 |
| 2005/0075550 | A1 | 4/2005 | Lindekugel | GB | 2 259 545 | 3/1993 |
| 2005/0085704 | A1 | 4/2005 | Schulz | JP | 63275325 A | 11/1988 |
| 2005/0090720 | A1 | 4/2005 | Wu | JP | 2013450 A | 1/1990 |
| 2005/0197548 | A1 | 9/2005 | Dietiker | JP | 2111343 A | 4/1990 |
| 2005/0228248 | A1 | 10/2005 | Dietiker | JP | 02 191434 | 7/1990 |
| 2005/0256386 | A1 | 11/2005 | Chan | JP | 2237544 A | 9/1990 |
| 2005/0272986 | A1 | 12/2005 | Smith | JP | 03 173536 | 7/1991 |
| 2005/0277819 | A1 | 12/2005 | Kiani et al. | JP | 3170866 A | 7/1991 |
| 2006/0020179 | A1 | 1/2006 | Anderson | JP | 3245042 A | 10/1991 |
| 2006/0030764 | A1 | 2/2006 | Porges | JP | 4174648 A | 6/1992 |
| 2006/0058594 | A1 | 3/2006 | Ishizuka et al. | JP | 4191642 A | 7/1992 |
| 2006/0074280 | A1 | 4/2006 | Martis | JP | 4332536 A | 11/1992 |
| 2006/0084852 | A1 | 4/2006 | Mason et al. | JP | 3124073 B | 3/1993 |
| 2006/0084878 | A1 | 4/2006 | Banet | JP | 5049624 A | 3/1993 |
| 2006/0089547 | A1 | 4/2006 | Sarussi | JP | 5049625 A | 3/1993 |
| 2006/0106294 | A1 | 5/2006 | Maser et al. | JP | 3115374 B | 4/1993 |
| 2006/0122517 | A1 | 6/2006 | Banet | JP | 2005/200031 | 8/1993 |
| 2006/0129039 | A1 | 6/2006 | Lindner | JP | 5212016 A | 8/1993 |
| 2006/0155198 | A1 | 7/2006 | Schmid | JP | 06014906 | 1/1994 |
| 2006/0173257 | A1 | 8/2006 | Nagai | JP | 6016774 B2 | 3/1994 |
| 2007/0032710 | A1 | 2/2007 | Raridan et al. | JP | 3116255 B | 4/1994 |
| 2007/0032712 | A1 | 2/2007 | Raridan et al. | JP | 6029504 U | 4/1994 |
| 2007/0032715 | A1 | 2/2007 | Eghbal et al. | JP | 6098881 A | 4/1994 |
| 2007/0073126 | A1 | 3/2007 | Raridan, Jr. | JP | 06 154177 | 6/1994 |
| 2008/0076987 | A1* | 3/2008 | Arizaga Ballesteros ..... 600/323 | JP | 6269430 A | 9/1994 |
| | | | | JP | 6285048 A | 10/1994 |

FOREIGN PATENT DOCUMENTS

| | | | | | |
|---|---|---|---|---|---|
| DE | 3516338 | 11/1986 | JP | 7001273 B2 | 1/1995 |
| DE | 37 03 458 | 8/1988 | JP | 7124138 A | 5/1995 |
| DE | 3938759 | 5/1991 | JP | 7136150 A | 5/1995 |
| DE | 4210102 A1 | 9/1993 | JP | 3116259 B | 6/1995 |
| DE | 4423597 | 8/1995 | JP | 3116260 B | 6/1995 |
| DE | 19632361 | 2/1997 | JP | 7155311 A | 6/1995 |
| DE | 69123448 | 5/1997 | JP | 7155313 A | 6/1995 |
| DE | 19703220 | 7/1997 | JP | 3238813 B2 | 7/1995 |
| DE | 19640807 A1 | 9/1997 | JP | 7171139 A | 7/1995 |
| DE | 19647877 A1 | 4/1998 | JP | 3134144 B | 9/1995 |
| DE | 10030862 | 1/2002 | JP | 7236625 A | 9/1995 |
| DE | 20318882 U1 | 4/2004 | JP | 7246191 A | 9/1995 |
| EP | 0127947 | 5/1984 | JP | 8256996 A | 10/1996 |
| EP | 00194105 B1 | 9/1986 | JP | 9192120 A | 7/1997 |
| EP | 00204459 A3 | 12/1986 | JP | 10216113 A | 8/1998 |
| EP | 0 262 779 | 4/1988 | JP | 10216114 A | 8/1998 |
| EP | 0315040 | 10/1988 | JP | 10216115 A | 8/1998 |
| EP | 0314331 | 5/1989 | JP | 10337282 A | 12/1998 |
| EP | 00352923 A1 | 1/1990 | JP | 11019074 A | 1/1999 |
| EP | 0 360 977 | 4/1990 | JP | 11155841 A | 6/1999 |
| EP | 00430340 A3 | 6/1991 | JP | 11 188019 | 7/1999 |
| EP | 0435 500 | 7/1991 | JP | 11244268 A | 9/1999 |
| EP | 0572684 | 5/1992 | JP | 20107157 A | 4/2000 |
| EP | 00497021 A1 | 8/1992 | JP | 20237170 A | 9/2000 |
| EP | 0529412 | 8/1992 | JP | 21245871 A | 9/2001 |
| EP | 0531631 | 9/1992 | JP | 22224088 A | 8/2002 |
| EP | 0566354 | 4/1993 | JP | 22282242 A | 10/2002 |
| EP | 0587009 | 8/1993 | JP | 23153881 A | 5/2003 |
| EP | 00630203 B1 | 9/1993 | JP | 23153882 A | 5/2003 |
| EP | 0 572 684 | 12/1993 | JP | 23169791 A | 6/2003 |
| EP | 00615723 A1 | 9/1994 | JP | 23194714 A | 7/2003 |
| EP | 00702931 A1 | 3/1996 | JP | 23210438 A | 7/2003 |
| EP | 00724860 A1 | 8/1996 | JP | 23275192 A | 9/2003 |
| EP | 00793942 A3 | 9/1997 | JP | 23339678 A | 12/2003 |
| EP | 0 864 293 | 9/1998 | JP | 24008572 A | 1/2004 |
| EP | 01006863 B1 | 10/1998 | JP | 24089546 A | 3/2004 |
| EP | 01006864 B1 | 10/1998 | JP | 24113353 A | 4/2004 |
| EP | 0875199 | 11/1998 | JP | 24135854 A | 5/2004 |
| EP | 00998214 A1 | 12/1998 | JP | 24148069 A | 5/2004 |
| EP | 0898933 | 3/1999 | JP | 24148070 A | 5/2004 |
| EP | 01332713 A1 | 8/2003 | JP | 24159810 A | 6/2004 |
| EP | 01469773 A1 | 8/2003 | JP | 24166775 A | 6/2004 |
| EP | 1502529 | 7/2004 | JP | 24194908 A | 7/2004 |
| | | | JP | 24202190 A | 7/2004 |
| | | | JP | 24248819 A | 9/2004 |

| | | |
|---|---|---|
| JP | 24248820 A | 9/2004 |
| JP | 24261364 A | 9/2004 |
| JP | 24290412 A | 10/2004 |
| JP | 24290544 A | 10/2004 |
| JP | 24290545 A | 10/2004 |
| JP | 24329406 A | 11/2004 |
| JP | 24329607 A | 11/2004 |
| JP | 24329928 A | 11/2004 |
| JP | 24337605 A | 12/2004 |
| JP | 24344367 A | 12/2004 |
| JP | 24351107 A | 12/2004 |
| JP | 25034472 A | 2/2005 |
| WO | WO 98/09566 A1 | 10/1989 |
| WO | WO 90/001293 A1 | 2/1990 |
| WO | WO 90/04352 | 5/1990 |
| WO | WO 91/01678 A1 | 2/1991 |
| WO | WO 91/11137 A1 | 8/1991 |
| WO | WO 92/00513 | 1/1992 |
| WO | WO 92/21281 A1 | 12/1992 |
| WO | WO 93/09711 | 5/1993 |
| WO | WO 93/13706 A2 | 7/1993 |
| WO | WO 93/16629 A1 | 9/1993 |
| WO | WO 94/03102 A1 | 2/1994 |
| WO | WO 94/23643 A1 | 10/1994 |
| WO | WO 95/02358 | 1/1995 |
| WO | WO 95/12349 A1 | 5/1995 |
| WO | WO 95/16970 | 6/1995 |
| WO | WO 96/13208 | 5/1996 |
| WO | WO 96/39927 A1 | 12/1996 |
| WO | WO 97/36536 | 10/1997 |
| WO | WO 97/36538 | 10/1997 |
| WO | WO 97/49330 A1 | 12/1997 |
| WO | WO 98/17174 A1 | 4/1998 |
| WO | WO 98/18382 | 5/1998 |
| WO | WO 98/43071 A1 | 10/1998 |
| WO | WO 98/51212 A1 | 11/1998 |
| WO | WO 98/57577 A1 | 12/1998 |
| WO | WO 99/00053 | 1/1999 |
| WO | WO 99/32030 A1 | 7/1999 |
| WO | WO 99/47039 A1 | 9/1999 |
| WO | WO 99/63884 | 12/1999 |
| WO | WO 00/21438 A1 | 4/2000 |
| WO | WO 00/28888 A1 | 5/2000 |
| WO | WO 00/59374 A1 | 10/2000 |
| WO | WO 01/13790 | 3/2001 |
| WO | WO 01/17421 A1 | 3/2001 |
| WO | WO 01/47426 | 3/2001 |
| WO | WO 0116577 | 3/2001 |
| WO | WO 01/40776 A1 | 6/2001 |
| WO | WO 01/67946 | 9/2001 |
| WO | WO 01/76461 A1 | 10/2001 |
| WO | WO 02/14793 A3 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 A1 | 1/2003 |
| WO | WO 03/001180 | 1/2003 |
| WO | WO 03/009750 A3 | 2/2003 |
| WO | WO 03/011127 A1 | 2/2003 |
| WO | WO 03/020129 | 3/2003 |
| WO | WO 03/039326 A3 | 5/2003 |
| WO | WO 03/063697 | 8/2003 |
| WO | WO 03/063697 A1 | 8/2003 |
| WO | WO 03/073924 A1 | 9/2003 |
| WO | WO 2004/000114 | 12/2003 |
| WO | WO 2004/006748 A3 | 1/2004 |
| WO | WO 2004/069046 | 8/2004 |
| WO | WO 2004/075746 A2 | 9/2004 |
| WO | WO 2005/002434 | 1/2005 |
| WO | WO 2005/009221 A2 | 2/2005 |
| WO | WO 2005/010567 A2 | 2/2005 |
| WO | WO 2005/010568 A3 | 2/2005 |
| WO | WO 2005/020120 A2 | 3/2005 |
| WO | WO 2005/065540 | 7/2005 |
| WO | WO 2006/104790 | 10/2006 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615. (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19$^{th}$ International Conference IEEE/EMBS*, Oct. 30$^{th}$ - Nov. 2$^{nd}$, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19$^{th}$ International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor, " *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20$^{th}$ annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20$^{th}$ Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Atlanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelback-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22$^{nd}$ Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, p. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Artificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceedings of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is a sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

R. Neumann, et al.; "Fourier Artifact suppression Technology Provides Reliable $SpO_2$," *Abstracts*, A11, p. S105. (undated).

Hamilton, Patrick S., et al.; "Effect of Adaptive Motion-Artifact Reduction on QRS Detection," *Biomedical Instrumentation &Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifacts Resistant Pulse Oximeter (Durapulse PA 2100)," *Journal of Oral Cavity Medicine*, vol. 69, No. 4, p. 53 (date unknown) (Article in Japanese—contains English summary of article).

\* cited by examiner

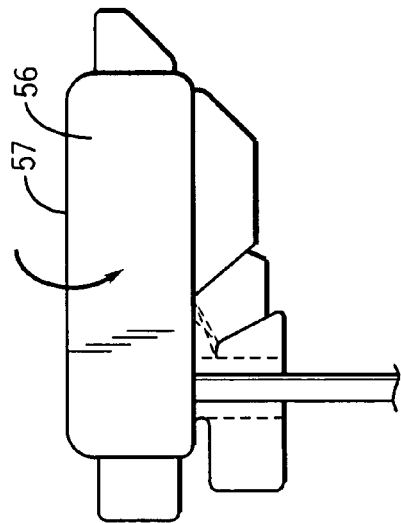
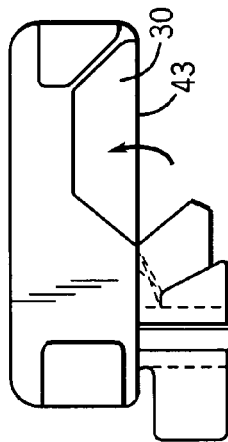
FIG. 7A    FIG. 7B
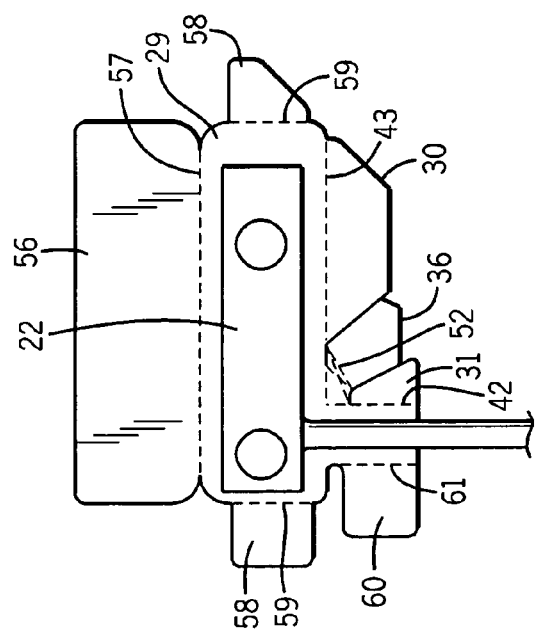
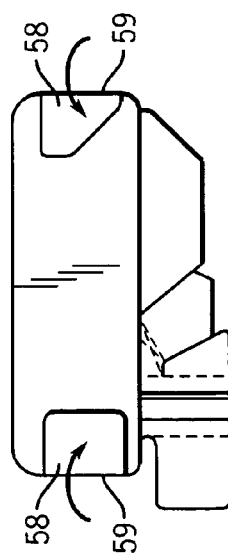
FIG. 7C    FIG. 7D

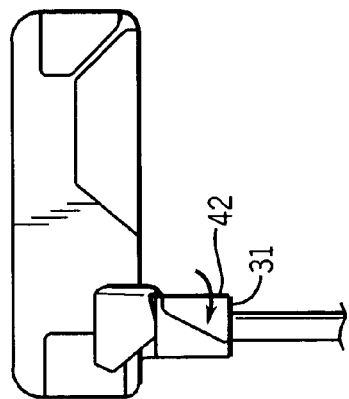

FLEXIBLE MEDICAL SENSOR ENCLOSURE

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is secured with adhesives and is reusable. To facilitate this requirement, pulse oximeters may be assembled by wrapping a sensor in a flexible material. The wrapped sensor may then be secured to a cover material that is used to affix the wrapped sensor to the patient. Finally a packaging film may be applied over the adhesive and cover materials to protect the adhesive portion prior to the application of the sensor to the patient.

Such adhesive and reusable sensors, however, may be subject to stresses during unpackaging, application, and use. For example, when the film covering of an oximetry sensor, such as a neonate sensor, is removed before application, the force of pulling away the film from the adhesive may cause stresses in the flexible material that cause the flexible material to tear. Tears in the flexible wrapping material may expose portions of the pulse oximeter sensor's circuitry and decrease the sensor's performance. These tears may be more common in corners of the flexible material where the stresses of pulling on the sensor are at their highest. As a further example, after the sensor is attached to the patient, stresses due to movement of the patient or the sensor may also lead to tears in the flexible material.

Also, it is desirable that the pulse oximeter sensor be assembled in a manner that eliminates exposure of the sensor's circuitry. Exposure of the sensor circuitry may lead to apprehension by the end user, and exposed circuitry may be susceptible to external sources of interference that may decrease the performance of the sensor. Therefore, the reusable sensor should be assembled in a manner that provides for complete enclosure of the pulse oximeter's circuitry. For example, when a pulse oximeter is assembled, the flexible material wrapped around the sensor should cover all portions of the pulse oximeter sensor. More specifically, when the flexible material is wrapped around the sensor, corner regions should not be void of material due to folds into adjacent areas.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a sensor enclosure assembly, comprising: a substrate, comprising: a plurality of fastening flaps; and a reinforcing flap, wherein the fastening flaps are folded about primary fold lines, wherein the primary fold lines, or their projections, intersect to form a corner, and wherein the reinforcing flap spans a region near the corner not covered by the folded fastening flaps when the reinforcing flap is folded.

In accordance with another aspect of the present invention, there is provided a sensor assembly, comprising: a sensor; and a sensor enclosure assembly, comprising; a substrate, comprising: a plurality of fastening flaps; and a reinforcing flap, wherein the fastening flaps are folded about primary fold lines, wherein the primary fold lines, or their projections, intersect to form a corner, and wherein the reinforcing flap spans a region near the corner not covered by the folded fastening flaps when the reinforcing flap is folded.

In accordance with yet another aspect of the present invention, there is provided a method of manufacturing a sensor assembly, the method comprising: affixing a sensor to a sensor enclosure, wherein the sensor enclosure comprises: fastening flaps; and at least one reinforcing flap; folding the fastening flaps about a sensor; and folding the reinforcing flap about the sensor.

BRIEF DESCRIPTION OF THE DRAWINGS

Advantages of the invention may become apparent upon reading the following detailed description and upon reference to the drawings in which:

FIG. 7A-7G illustrates a sequence of folding the modified flexible wrap to enclose a sensor, in accordance with aspects of the present technique.

DETAILED DESCRIPTION OF SPECIFIC EMBODIMENTS

Figure 1:
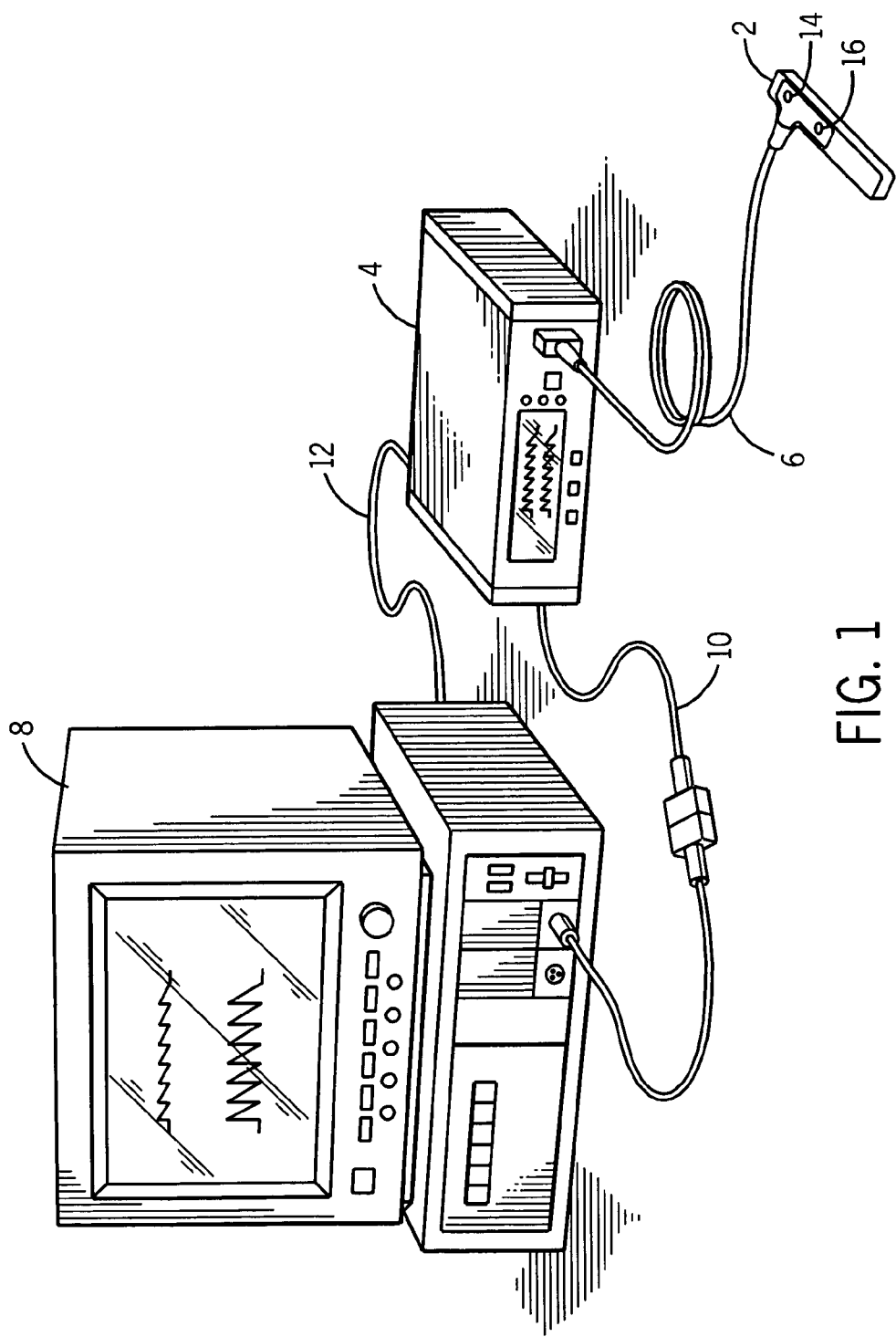
FIG. 1 illustrates a patient monitoring system coupled to a multi-parameter patient monitor and a sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and reusable patient sensor, such as for use in pulse oximetry or other applications utilizing spectrophotometry, that does not expose portions of the sensor's circuitry and that is resistant to tearing. In accordance with some aspects of the present technique, a reusable patient sensor is provided that is wrapped in a flexible material that prevents exposure of the sensor and that is resistant to tearing. The flexible material may include an additional flap of material that prevents exposure of the sensor circuitry and which may provide added strength to resist tearing of the flexible material.

Prior to discussing such exemplary sensors in detail, it should be appreciated that such sensors are typically designed for use with a patient monitoring system. For example, referring now to FIG. 1, a sensor 2 according to an exemplary embodiment may be used in conjunction with a patient monitor 4. In the depicted embodiment, a cable 6 connects the sensor 2 to the patient monitor 4. As will be appreciated by those of ordinary skill in the art, the sensor 2 and/or the cable 6 may include or incorporate one or more integrated circuit devices or electrical devices, such as a memory, processor chip, or resistor, that may facilitate or enhance communication between the sensor 2 and the patient monitor 4. Likewise the cable 6 may be an adaptor cable, with or without an integrated circuit or electrical device, for facilitating communication between the sensor 2 and various types of monitors, including older or newer versions of the patient monitor 4 or other physiological monitors. In other embodiments, the sensor 2 and the patient monitor 4 may communicate via wireless means, such as using radio, infrared, or optical signals. In such embodiments, a transmission device (not shown) may be connected to the sensor 2 to facilitate wireless transmission between the sensor 2 and the patient monitor 4. As will be appreciated by those of ordinary skill in the art, the cable 6 (or corresponding wireless transmissions) are typically used to transmit control or timing signals from the monitor 4 to the sensor 2 and/or to transmit acquired data from the sensor 2 to the monitor 4. In some embodiments, however, the cable 6 may be an optical fiber that allows optical signals to be conducted between the monitor 4 and the sensor 2.

In one embodiment, the patient monitor 4 may be a suitable pulse oximeter, such as those available from Nellcor Puritan Bennett Inc. In other embodiments, the patient monitor 4 may be a monitor suitable for measuring tissue water fractions, or other body fluid related metrics, using spectrophotometric or other techniques. Furthermore, the monitor 4 may be a multi-purpose monitor suitable for performing pulse oximetry and measurement of tissue water fraction, or other combinations of physiological and/or biochemical monitoring processes, using data acquired via the sensor 2. Furthermore, to upgrade conventional monitoring functions provided by the monitor 4 to provide additional functions, the patient monitor 4 may be coupled to a multi-parameter patient monitor 8 via a cable 10 connected to a sensor input port and/or via a cable 12 connected to a digital communication port.

The sensor 2, depicted in FIG. 1, is an adhesive style sensor that is flexible to conform to the surface of a patient's skin. The sensor 2 includes an emitter 14 and a detector 16 which may be of any suitable type. For example, the emitter 14 may be one or more light emitting diodes adapted to transmit one or more wavelengths of light, such as in the red to infrared range, and the detector 16 may be a photodetector, such as a silicon photodiode package, selected to receive light in the range emitted from the emitter 14. In the depicted embodiment, the sensor 2 is coupled to a cable 6 that is responsible for transmitting electrical and/or optical signals to and from the emitter 14 and detector 16 of the sensor 2. The cable 6 may be permanently coupled to the sensor 2, or it may be removably coupled to the sensor 2—the latter alternative being more useful and cost efficient in situations where the sensor 2 is disposable.

The sensor 2 described above is generally configured for use as a "transmission type" sensor for use in spectrophotometric applications, though in some embodiments it may instead be configured for use as a "reflectance type sensor." Transmission type sensors include an emitter 14 and detector 16 that are typically placed on opposing sides of the sensor site. If the sensor site is a fingertip, for example, the sensor 2 is positioned over the patient's fingertip such that the emitter 14 and detector 16 lie on either side of the patient's nail bed. For example, the sensor 2 is positioned so that the emitter 14 is located on the patient's fingernail and the detector 16 is located opposite the emitter 14 on the patient's finger pad. During operation, the emitter 14 shines one or more wavelengths of light through the patient's fingertip, or other tissue, and the light received by the detector 16 is processed to determine various physiological characteristics of the patient.

Reflectance type sensors generally operate under the same general principles as transmittance type sensors. However, reflectance type sensors include an emitter and detector that are typically placed on the same side of the sensor site. For example, a reflectance type sensor may be placed on a patient's fingertip such that the emitter and detector are positioned side-by-side. Reflectance type sensors detect light photons that are scattered back to the detector.

As described previously, the sensor 2 discussed herein may be configured for either transmission or reflectance type sensing. For simplicity, the exemplary embodiment of the sensor 2 described herein is adapted for use as a transmission-type sensor. As will be appreciated by those of ordinary skill in the art, however, such discussion is merely exemplary and is not intended to limit the scope of the present technique.

Figure 2:
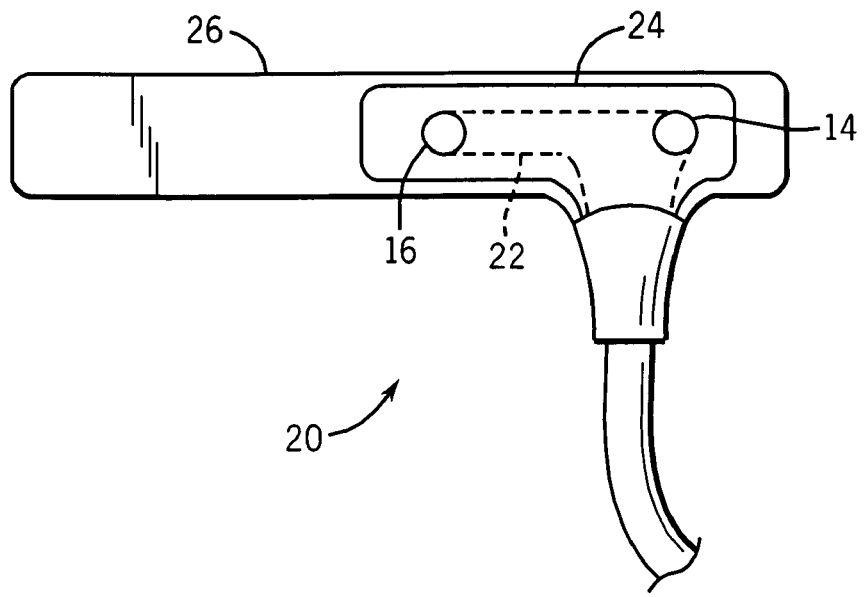
FIG. 2 illustrates a patient sensor assembly in accordance with aspects of the present technique.
Figure 3:
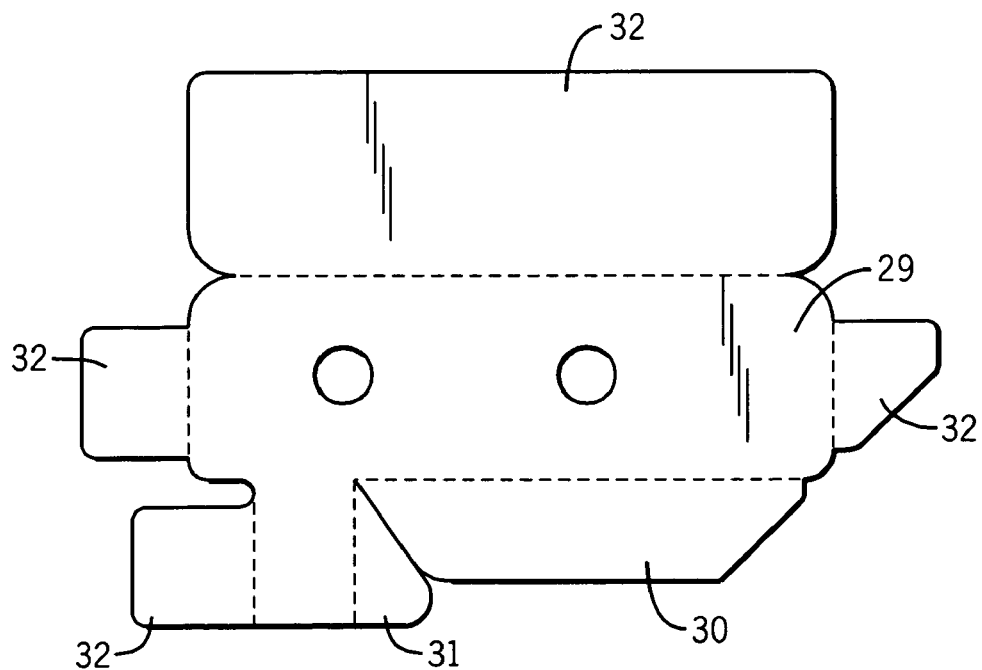
FIG. 3 illustrates a flexible wrap in accordance with aspects of the prior art.
Figure 4:
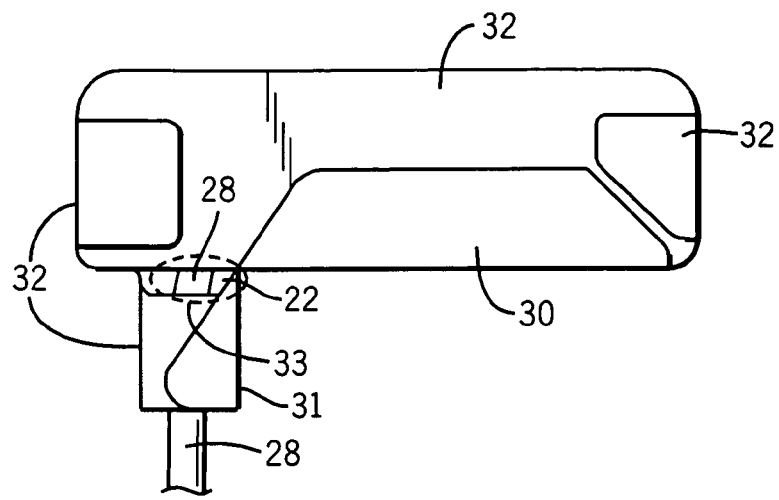
FIG. 4 illustrates a sensor assembly wherein the flexible wrap is folded about the sensor, and gap region remains that exposes sensor circuitry in accordance with aspects of the prior art.

Referring now to FIG. 2, a sensor assembly 20 is depicted. As shown, the sensor assembly 20 is a neonate transmission type sensor. Such a neonate sensor may include, for example, pulse oximeter sensor circuitry 22, which is enclosed within a flexible wrap 24, and which is secured to a patient by a bandage 26. Generally, a pulse oximeter sensor is assembled by enclosing the sensor circuitry 22 within the flexible wrap 24. The flexible wrap 24 is generally formed from a substrate, such as a sheet of plastic, that is cut into a shape that provides for the substrate to enclose and conform to the shape of the sensor circuitry 22, as depicted in FIG. 3. To enable a single sheet of two-dimensional substrate to enclose all sides of the sensor circuitry 22, the substrate shape may contain a bottom 29, as well as primary flaps 30, 31, and 32 which may be folded over the sensor circuitry 22 to enclose the sensor circuitry 22. However, generally, this procedure may result in folds which do not cover all portions of the sensor circuitry or sensor cable. For example, as depicted by FIG. 4, the primary flaps 30, 31, and 32 of flexible wrap 24 may be folded leaving a gap region 33 that does not provide for coverage a the sensor cable 28 or sensor circuitry 22. This gap region 33 may allow exposure of the sensor circuitry 22 and of a sensor cable 28. Further, the absence of material in the gap region 33 promotes localized stresses that may result in increased instances of tearing in or near the gap region 33.

Figure 5:
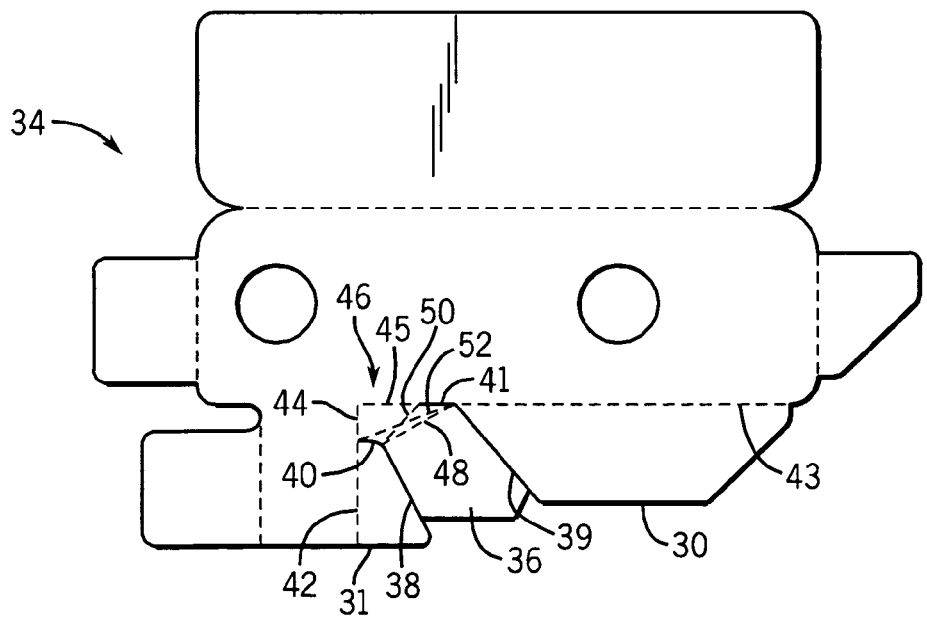
FIG. 5 illustrates a modified flexible wrap in accordance with aspects of the present technique.

Referring now to FIG. 5, a modified flexible wrap 34 is depicted. In the depicted example, the modified flexible wrap 34 includes a reinforcing flap 36 that may be folded over the sensor circuitry 22 to cover the gap region 33 (see FIG. 4) and to increase the flexible wrap's 34 resistance to tearing. Such a reinforcing flap 36 may include a variety of shapes and locations. For example, the reinforcing flap 36 may be located in a region between two primary flaps 30 and 31 and formed by reinforcing cuts 38 and 39. In one embodiment, the reinforcing cuts 38 and 39 may be aligned at angle not substantially parallel to the primary fold lines 42 and 43 about which the primary flaps 30 and 31 are folded. By making reinforcing cuts 38 and 39 that are not substantially parallel to the primary fold lines 42 and 43, there may be provided additional material to be used in forming the primary flaps 30 and 31 adjacent to the reinforcing flap 36. For example, as depicted in FIG. 5, the reinforcing cuts 38 and 39 are made at an angles that generally dissect the angle of the corner 46 formed by the projections 44 and 45 of the primary fold lines 42 and 43. It should be noted that, the angle of the reinforcing cut 38 provides for additional material available for the primary flap 31. The reinforcing flap 36 may then be folded about reinforcing fold line A 48, which is formed between the ends of the reinforcing cuts 38 and 39 nearest the corner 46.

In one embodiment, relief cuts 40 and 41 may be made at the ends of the reinforcing cuts 38 and 39 wherein the relief cuts 40 and 41 are not parallel to the reinforcing cuts 38 and 39. For example, as depicted in FIG. 5, the relief cuts 41 and 40 may be made from the ends of the reinforcing cuts 38 and 39 in a direction parallel to primary fold line 43. The relief cuts 40 and 41 provide for folding the reinforcing flap 36 in a multitude of angles without promoting tearing at the end of the reinforcing cuts 38 and 39 nearest the corner 46 or the relief cuts 40 and 41. For example, the relief cuts 40 and 41 provide for folding of the reinforcing flap 36 about multiple fold lines. As depicted, the reinforcing flap 36 may be folded about reinforcing fold line A 48, reinforcing fold line B 50, or reinforcing fold line C 52, or it may be folded at any angle between the reinforcing fold line B 50 and the reinforcing fold line C 52. As a person of ordinary skill in the art will appreciate, the length and angle of the reinforcing cuts 38 and 39 and the relief cuts 40 and 41 may be varied in number, length, angle, and shape to provide for the needs of various folding applications.

Figure 6:
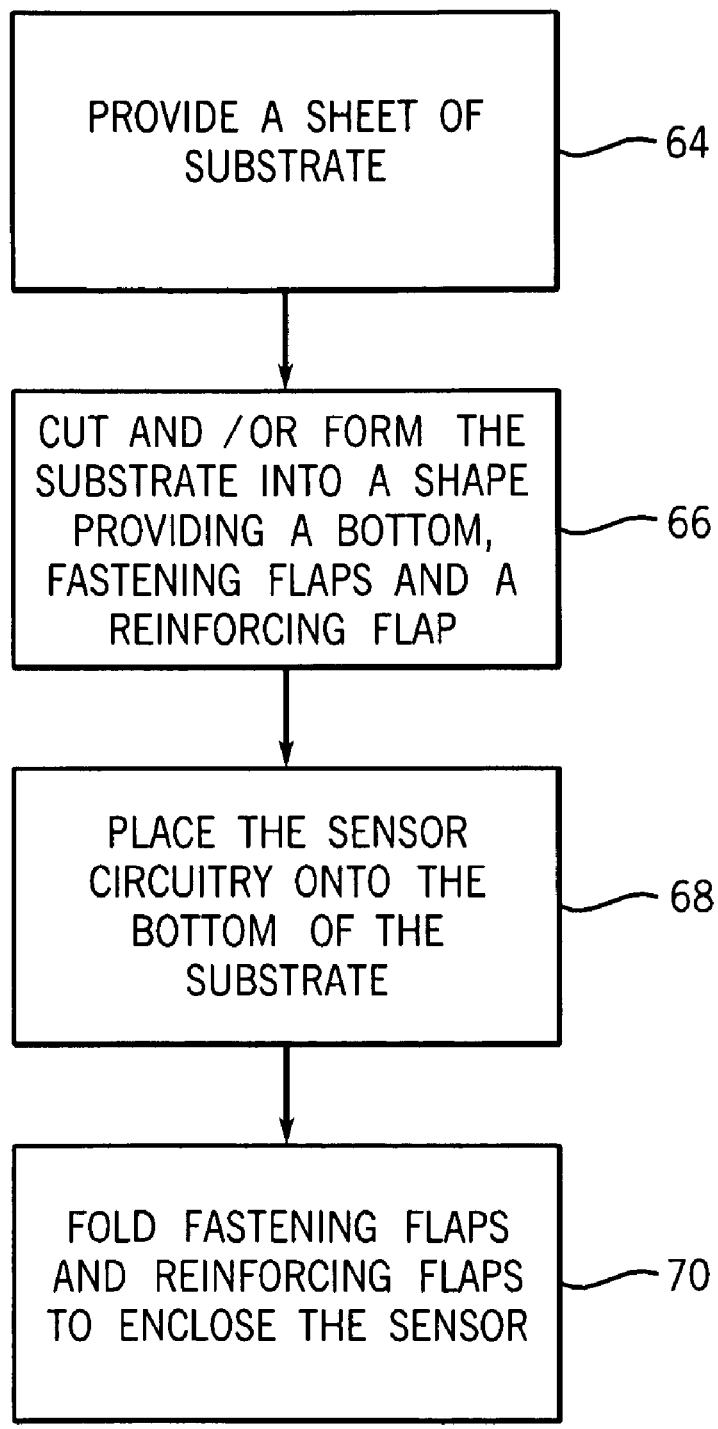
FIG. 6 depicts a flowchart of a method for cutting and assembling a modified flexible wrap about a sensor.

Turing now to FIG. 6, a flowchart of a method to assemble the flexible wrap 24 to the sensor circuitry 22 is depicted. First, a substrate of flexible wrap 24 may be provided (Block 64) from which the modified flexible wrap 24 may be shaped (Block 66). For example, a sheet of flexible wrap 24 may be provided and cut to shape of the modified flexible wrap 34, as depicted in FIG. 5. As will be appreciated by a person of ordinary skill in the art, the method of forming the modified flexible wrap 34 may be varied to accommodate various means of manufacture. For example, the flexible wrap 24 may include a single sheet of substrate cut to the shape of the modified flexible wrap 34, or the flexible wrap 24 may initially be formed in the shape of the modified flexible wrap 34, and require minimal or no modification. The sensor circuitry 22 may then be placed (Block 68) onto the bottom 29 of the modified flexible wrap 34. The primary folding flaps 30, 31 and 32 and reinforcing flap(s) 36 may be folded (Block 70) about the fold lines to enclose the sensor circuitry 22. For example, FIG. 7 depicts the method of manufacturing a pulse oximeter sensor by placing and wrapping sensor circuitry 22 in the modified flexible wrap 34. FIG. 7A depicts placing the sensor circuitry 22 on the bottom 29 of the modified flexible wrap 34. FIG. 7B depicts folding a top primary flap 56 about a top primary fold line 57. FIG. 7C depicts folding side primary flaps 58 about side primary fold lines 59. FIG. 7D depicts folding the primary flap 30 about the primary fold line 43. FIG. 7E depicts folding the reinforcing flap 36 about reinforcing fold line C 52. FIG. 7F depicts folding a lower primary flap 60 about a lower primary fold line 61. FIG. 7G depicts folding the primary flap 31 about a primary fold line 42. As will be appreciated by those ordinarily skilled in the art, the number and sequence of steps to enclose the sensor circuitry may vary to provide for various applications. For example, the sequence of folding the flaps as depicted in FIG. 7 may be varied in any sequence.

While the exemplary medical sensors 2 discussed herein are some examples of adhesive and disposable medical devices, other such devices are also contemplated and fall within the scope of the present disclosure. For example, other medical sensors and/or contacts applied externally to a patient may be advantageously applied using a modified flexible enclosure as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A sensor enclosure assembly, comprising:
    a substrate, comprising:
        a plurality of fastening flaps; and
        a reinforcing flap, wherein the fastening flaps are folded about primary fold lines, wherein the primary fold lines, or their projections, intersect to form a corner, and wherein the reinforcing flap spans a region near the corner not covered by the folded fastening flaps when the reinforcing flap is folded, wherein the reinforcing flap is created by at least one primary cut in the substrate, wherein the span between two of the ends of the primary cut forms a reinforcing fold line that is not substantially parallel to the primary fold lines, and wherein the reinforcing flap is folded about the reinforcing fold line.

2. The sensor enclosure assembly of claim 1, comprising a relief cut, wherein the relief cut extends from an end of the primary cut nearest the corner.

3. The sensor enclosure assembly of claim 2, wherein the relief cut extends in a direction substantially parallel to at least one of the primary fold lines.

4. The sensor enclosure assembly of claim 2, wherein the relief cut facilitates folding the reinforcing flap at multiple angles.

5. The sensor enclosure assembly of claim 1, wherein the reinforcing flap covers the complete region not covered by the fastening flaps when folded.

6. A sensor assembly, comprising:
    a sensor; and
    a sensor enclosure assembly, comprising;
        a substrate, comprising:
    a plurality of fastening flaps; and
    a reinforcing flap, wherein the fastening flaps are folded about primary fold lines, wherein the primary fold lines, or their projections, intersect to form a corner, and wherein the reinforcing flap spans a region near the corner not covered by the folded fastening flaps when the reinforcing flap is folded, wherein the reinforcing flap is created by at least one primary cut in the substrate, wherein the span between two of the ends of the primary cut, forms a reinforcing fold line that is not substantially parallel to the primary fold lines, and wherein the reinforcing flap is folded about the reinforcing fold line.

7. The sensor assembly of claim 6, comprising at least one relief cut, wherein the relief cut extends from the end of a primary cut nearest the corner.

8. The sensor assembly of claim 7, wherein the relief cut extends in a direction substantially parallel to at least one of the primary fold lines.

9. The sensor assembly of claim 7, wherein the relief cut facilitates folding the reinforcing flap in multiple directions.

10. The sensor assembly of claim 6, wherein the reinforcing flap covers the complete region not covered by the fastening flaps when folded.

11. The sensor assembly of claim 6, wherein the reinforcing flap covers exposed portions of the sensor when folded.

12. The sensor assembly of claim 6, further comprising a material affixed to the sensor enclosure, wherein the material provides for attachment of the sensor assembly to a surface.

13. A method of manufacturing a sensor assembly, the method comprising:
    affixing a sensor to a sensor enclosure, wherein the sensor enclosure comprises:
        fastening flaps; and
        at least one reinforcing flap;
    folding the fastening flaps about the sensor; and
    folding the reinforcing flap about the sensor, wherein folding the reinforcing flap about the sensor comprises folding the reinforcing flap about a reinforcing fold line, wherein the reinforcing fold line is the span between ends of at least one primary cut that creates the shape of the reinforcing flap, and wherein the reinforcing fold line is not substantially parallel to a fold line of the fastening flaps.

14. The method of claim 13, wherein the sensor is a pulse oximeter sensor.

15. The method of claim 14, comprising folding the fastening flaps prior to folding the reinforcing flap about the sensor.

16. The method of claim 13, wherein material is affixed to the sensor enclosure, to provide for attachment of the sensor assembly to a surface.

17. A method of manufacturing a sensor assembly, the method comprising:
    affixing a sensor to a sensor enclosure, wherein the sensor enclosure comprises:
        fastening flaps; and
        at least one reinforcing flap;
    folding the fastening flaps about the sensor; and
    folding the reinforcing flap about the sensor, wherein folding the reinforcing flap about the sensor comprises folding the reinforcing flap about a reinforcing fold line, wherein the reinforcing fold line is the span between the end of a primary cut and a relief cut, or between two relief cuts, wherein the primary cut creates the shape of the reinforcing flap, wherein the relief cut extends from the end of a primary cut, and wherein the reinforcing fold line is not substantially parallel to a fold line of the fastening flap.

* * * * *